US00PP26204P3

(12) United States Plant Patent
Zaiger et al.

(10) Patent No.: US PP26,204 P3
(45) Date of Patent: Dec. 15, 2015

(54) INTERSPECIFIC TREE NAMED 'CRIMSON ROSE'

(50) Latin Name: **Interspecific *Prunus* species**
Varietal Denomination: Crimson Rose

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 210 days.

(21) Appl. No.: 13/998,845

(22) Filed: Dec. 16, 2013

(65) Prior Publication Data

US 2015/0173267 P1 Jun. 18, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Fruit with attractive red skin and flesh color.
3. Fruit with very good flavor and eating quality.
4. Fruit with good handling and shipping quality.
5. Fruit with an average Brix of 18.5°.
6. Heavy and regular production of fruit.

1 Drawing Sheet

Botanical designation: Interspecific *Prunus* species.
Variety denomination: 'Crimson Rose'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of non-patented proprietary interspecific trees, which are known to us, and mentioned herein, '110LT266', '317LH222', '11ZB482' and the Interspecific 'Flavor Fusion' (U.S. Plant Pat. No. 23,902).

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses between the following species [*Prunus salicina*×(*Prunus salicina*×*Prunus armeniaca*)]. The present variety is a seedling from our open pollinated proprietary interspecific seedling with the field identification number '110LT266' (non-patented). The seed parent (110LT266) (non-patented) is a first generation cross from our non-patented proprietary interspecific seedling selections '317LH222' and '11ZB482'. We budded a large number of these seedlings to older trees of 'Nemaguard' Rootstock (non-patented) to induce earlier fruit production for evaluation. Under close and careful observation, one seedling, which is the present variety exhibited desirable fruit and tree characteristics and was selected in 2006 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which includes plums and plumcots in its parentage, is of large size, vigorous, upright growth and a productive and regular bearer of medium to large size fruit with very good flavor and eating quality. The fruit is further characterized by having attractive red skin, firm, red flesh and having good shipping and storage quality. In comparison to its non-patented interspecific seed parent '110LT266' the fruit of the new variety has red compared to yellow flesh and is approximately 30 days later in maturity. In comparison to the commercial Interspecific 'Flavor Fusion' (U.S. Plant Pat. No. 23,902) the fruit of the variety is approximately 25 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size.*—Large, usually pruned to 3 to 3.5 meters in height and width for economical harvesting of fruit.

*Vigor.*—Vigorous, tree growth of approximately 1.5 to 2 meters the first growing season, varies with soil type, fertility and cultural practices.

*Form.*—Upright, usually pruned to vase shape.

*Branching habit.*—Upright, crotch angle approximately 30°, increases with heavy crop load.

*Productivity.*—Productive, thinning and spacing necessary for desired market size fruit. Fruit set varies with climatic conditions at bloom time.

*Bearer.*—Regular, has had adequate fruit set 5 consecutive years. No alternate bearing observed.

*Fertility.*—Self sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

Trunk:

*Size.*—Medium to large. Average circumference 44.5 cm at 30.5 cm above ground on a 7 year old tree.

*Stocky.*—Medium stocky.

*Texture.*—Medium shaggy, roughness increases with age.

*Color.*—Varies from 5Y 4/2 to 5Y 2/2.

Branches:

*Size.*—Medium. Average circumference 11.9 cm at 1.2 meters above ground. Crotch angle approximately 30°, increases with heavy crop load.

*Surface texture.*—New growth relatively smooth. Mature growth medium rough, roughness increases with age.

*Lenticels.*—Average number 53 in a 25.8 sq cm section. Average length 3.1 mm. Average width 1.3 mm. Color varies from 10YR 5/8 to 10YR 5/10.

*Color.*—New growth varies from 5GY 4/8 to 5GY 5/6. Mature growth varies from 7.5YR 2/4 to 10YR 2/2, varies with age of growth.

Leaves:

*Size.*—Medium. Average length 87.7 mm. Average width 38.8 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and pinnate venation, glabrous. Lower surface relatively smooth except for small ridges created by midrib and pinnate venation, glabrous.

*Petiole.*—Average length 11.5 mm. Average width 1.5 mm. Longitudinally grooved. Surface — glabrous. Color varies from 2.5GY 7/6 to 2.5GY 6/6.

*Glands.*—Globose. Size — small. Average length 0.6 mm. Average diameter 0.2 mm. Average number 2, varies from 1 to 2. Located primarily on the upper portion of the petiole and the base of the leaf blade. Color varies from 7.5YR 3/6 to 7.5YR 3/4.

*Stipules.*—Average number 2. Average length 7.6 mm. Edges — pectinate. Color varies from 5GY 7/6 to 5GY 6/6.

*Color.*—Upper surface varies from 7.5GY 3/4 to 10GY 2/4. Lower surface varies from 7.5GY 4/4 to 10GY 4/4. Midvein color varies from 2.5GY 7/4 to 5GY 7/4.

Flower buds:

*Size.*—Small to medium. Average length 8.8 mm. Average diameter 5.0 mm.

*Hardiness.*—Hardy with respect to California winters.

*Form.*—Conical, becoming elongated before opening.

*Pedicel.*—Average length 9.4 mm. Average width 0.8 mm. Color varies from 10Y 8/6 to 2.5GY 7/6. Surface — glabrous.

*Color.*—N 9.5/(white).

*Number of buds per spur.*—Average number 12, varies with age of spur.

Flowers:

*Blooming period.*—Date of First Bloom Feb. 23, 2013. Date of Petal Fall Mar. 5, 2013, varies slightly with climatic conditions.

*Size.*—Small to medium. Average height 11.2 mm. Average diameter 19.5 mm.

*Petals.*—Size — small to medium. Number — normally 5, alternately arranged to the sepals. Average length 10.1 mm. Average width 8.1 mm. Form — orbicular, narrowing at point of attachment. Margin — sinuate. Color N 9.5/(white). Both upper and lower surfaces glabrous. Arrangement — free.

*Sepals.*—Size — small. Number — normally 5, alternately arranged to the petals. Average length 2.4 mm. Average width 2.4 mm. Form — triangular. Margin — entire. Color — upper surface varies from 2.5GY 7/8 to 5GY 7/6. Lower surface varies from 2.5GY 6/6 to 5GY 7/8. Both upper and lower surfaces glabrous.

*Stamens.*—Average number per flower 30. Average filament length 7.8 mm. Filament color N 9.5/(white). Anther color varies from 5Y 8.5/8 to 5Y 8/8.

*Pollen.*—Self-sterile, pollinator required. Color varies from 2.5Y 7/12 to 5Y 7/12.

*Pistil.*—Normally 1. Surface — glabrous. Average length 6.9 mm. Stigma height approximately 1.7 mm below anthers. Color varies from 10Y 8.5/4 to 2.5GY 8/4.

*Fragrance.*—Heavy aroma.

*Color.*—N 9.5/(white).

*Pedicel.*—Average length 9.9 mm. Average width 0.8 mm. Color varies from 10Y 7/6 to 2.5GY 8/6. Surface — glabrous.

*Number flowers per flower bud.*—Average number 2, varies from 1 to 4.

Fruit:

*Maturity when described.*—Firm ripe.

*Date of first picking.*—Jul. 10, 2013.

*Date of last picking.*—Jul. 18, 2013, varies slightly with climatic conditions.

*Size.*—Medium to large. Average diameter axially 53.4 mm. Average transversely in suture plane 54.9 mm. Average weight 119.5 grams, varies slightly with fertility of the soil, amount of thinning and climatic conditions.

*Form.*—Globose to slightly elongated.

*Suture.*—Nearly smooth, extends from base to apex.

*Ventral surface.*—Very slightly lipped.

*Apex.*—Rounded to slightly pointed.

*Base.*—Flat.

*Stem cavity.*—Rounded to slightly elongated in suture plane. Average depth 4.0 mm. Average diameter 10.1 mm.

Stem:

*Size.*—Medium. Average length 11.9 mm. Average diameter 1.7 mm.

*Color.*—10Y 7/6.

Skin:

*Thickness.*—Medium.

*Surface.*—Smooth.

*Bloom.*—Moderate amount, complete coverage.

*Tendency to crack.*—None.

*Color.*—Ground color varies from 5Y 8/4 to 7.5Y 8/2. Overspread with 5R 3/6 to 7.5R 2/2.

*Tenacity.*—Tenacious to flesh.

*Astringency.*—Undetected.

Flesh:

*Ripens.*—Evenly.

*Texture.*—Firm, meaty.

*Fibers.*—Few, small, tender.

*Firmness.*—Firm, comparable to other commercial interspecific varieties.

*Aroma.*—Slight.

*Amydgalin.*—Undetected.

*Eating quality.*—Very good.

*Flavor.*—Very good, a good balance between acid and sugar.

*Juice.*—Moderate amount, enhances flavor.

*Brix.*—Average Brix 18.5°, varies slightly with amount of fruit per tree and climatic conditions.

*Color.*—Varies from 5R 3/8 to 7.5R 3/10.

*Pit cavity.*—Average length 28.8 mm. Average width 18.4 mm. Average depth 11.4 mm. Color varies from 7.5R 3/6 to 10R 3/6.

Stone:

*Type.*—Clingstone.

*Size.*—Medium. Average length 23.4 mm. Average width 17.4 mm. Average thickness 9.4 mm.

*Form.*—Ovoid.

*Base.*—Relatively flat, varies from flat to rounded.

*Apex.*—Pointed. Average length 1.4 mm.

*Surface.*—Slightly pitted throughout. A small groove on each side of suture.

*Sides.*—Unequal, one side extending further from suture plane.

*Ridges.*—Small, narrow ridges extending from base to apex.

*Tendency to split.*—None.

*Color.*—Varies from 10YR 7/6 to 10YR 6/6 when dry.

Kernel:

*Size.*—Medium. Average length 15.9 mm. Average width 9.9 mm. Average depth 4.4 mm.

*Form.*—Ovoid.

*Viability.*—Partial viability, some embryos not fully developed.

*Skin color.*—Varies from 2.5Y 9/4 to 2.5Y 8.5/4.

Use: Dessert.

*Market.*—Local and long distance.

Keeping quality: Good, held firm in cold storage for 3 weeks at 38° to 42° F. without internal breakdown of flesh or appreciable loss of flavor.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

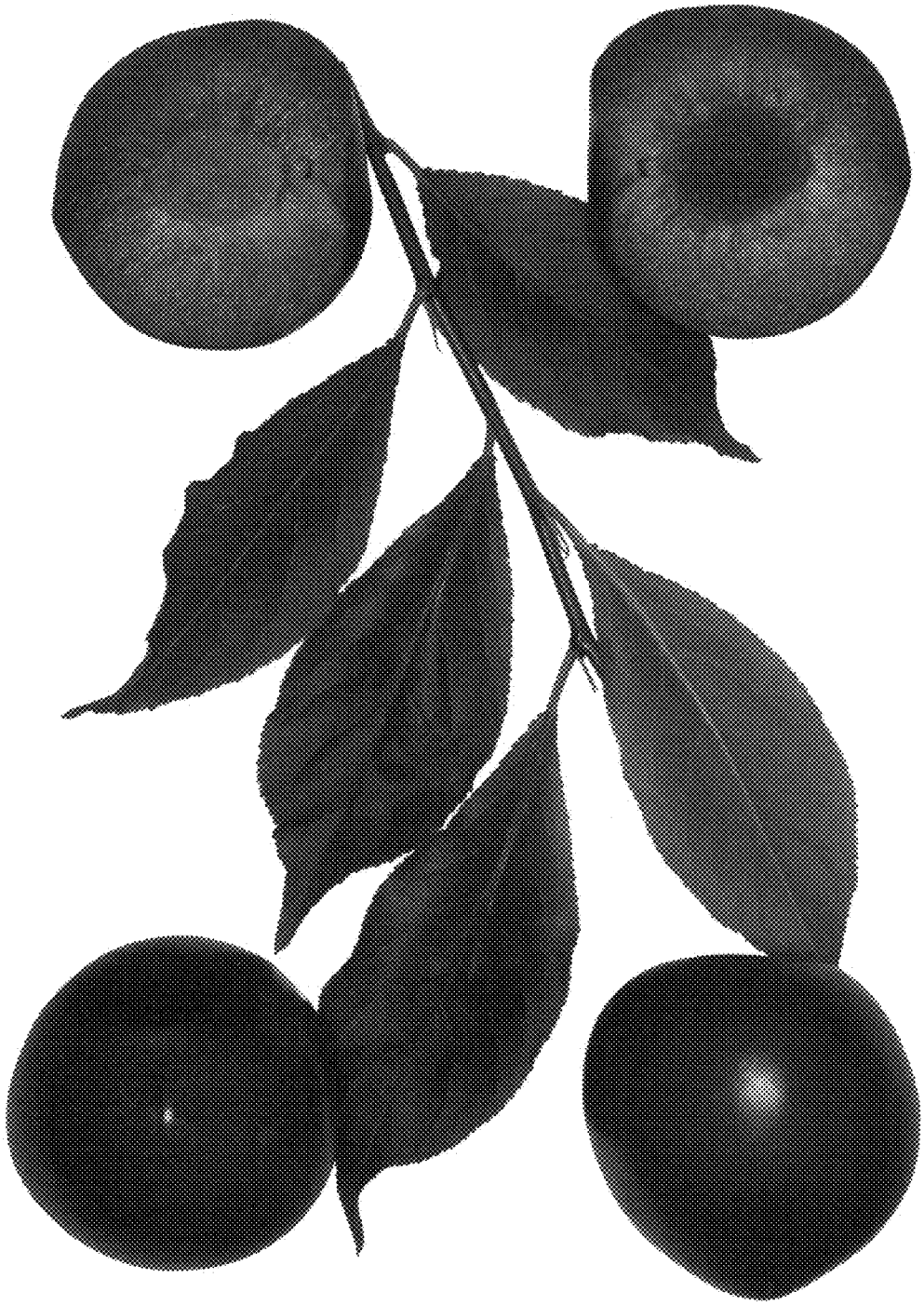

* * * * *